(12) United States Patent
Wang et al.

(10) Patent No.: US 9,554,881 B2
(45) Date of Patent: Jan. 31, 2017

(54) COLORING SOLUTION FOR DENTAL ZIRCONIA CERAMICS AND METHOD FOR USING THE SAME

(71) Applicant: SHENZHEN UPCERA DENTAL TECHNOLOGY CO., LTD, Shenzhen (CN)

(72) Inventors: Hongjuan Wang, Benxi (CN); Qingyun Yan, Benxi (CN); Dongbin Huang, Shenzhen (CN); Lingling He, Benxi (CN); Yanchun Zheng, Benxi (CN)

(73) Assignee: SHENZHEN UPCERA DENTAL TECHNOLOGY CO., LTD., Shenzhen (CN)

( * ) Notice: Subject to any disclaimer, the term of this patent is extended or adjusted under 35 U.S.C. 154(b) by 116 days.

(21) Appl. No.: 14/397,449

(22) PCT Filed: Apr. 28, 2013

(86) PCT No.: PCT/CN2013/074962
§ 371 (c)(1),
(2) Date: Oct. 27, 2014

(87) PCT Pub. No.: WO2013/170705
PCT Pub. Date: Nov. 21, 2013

(65) Prior Publication Data
US 2015/0122147 A1    May 7, 2015

(30) Foreign Application Priority Data

May 15, 2012    (CN) .......................... 2012 1 0149521
Dec. 20, 2012   (CN) .......................... 2012 1 0558349

(51) Int. Cl.
| | | |
|---|---|---|
| C04B 41/85 | (2006.01) | |
| A61C 13/08 | (2006.01) | |
| C04B 41/00 | (2006.01) | |
| C04B 41/50 | (2006.01) | |
| C08K 3/16 | (2006.01) | |
| C08K 3/28 | (2006.01) | |
| C08K 5/098 | (2006.01) | |
| A61K 6/02 | (2006.01) | |
| C04B 35/486 | (2006.01) | |
| A61K 6/00 | (2006.01) | |
| C04B 35/626 | (2006.01) | |
| C04B 35/634 | (2006.01) | |
| C04B 35/636 | (2006.01) | |
| C04B 111/00 | (2006.01) | |
| C04B 111/82 | (2006.01) | |
| C04B 111/80 | (2006.01) | |

(52) U.S. Cl.
CPC .......... *A61C 13/082* (2013.01); *A61K 6/0094* (2013.01); *A61K 6/024* (2013.01); *A61K 6/025* (2013.01); *C04B 35/486* (2013.01); *C04B 35/62625* (2013.01); *C04B 35/634* (2013.01); *C04B 35/636* (2013.01); *C04B 41/009* (2013.01); *C04B 41/5007* (2013.01); *C04B 41/85* (2013.01); *C08K 3/16* (2013.01); *C08K 3/28* (2013.01); *C08K 5/098* (2013.01); *C04B 2111/00836* (2013.01); *C04B 2111/80* (2013.01); *C04B 2111/82* (2013.01); *C04B 2235/3224* (2013.01); *C04B 2235/3229* (2013.01); *C04B 2235/44* (2013.01); *C04B 2235/443* (2013.01); *C04B 2235/444* (2013.01); *C04B 2235/448* (2013.01); *C04B 2235/449* (2013.01); *C04B 2235/606* (2013.01); *C04B 2235/616* (2013.01); *C04B 2235/6567* (2013.01); *C04B 2235/96* (2013.01); *C04B 2235/9653* (2013.01); *C04B 2235/9661* (2013.01)

(58) Field of Classification Search
CPC ...... A61C 13/082; A61K 6/0094; C04B 41/85
See application file for complete search history.

(56) References Cited

U.S. PATENT DOCUMENTS

| | | | | |
|---|---|---|---|---|
| 6,709,694 B1 * | 3/2004 | Suttor | .................. | A61K 6/0094 427/2.1 |
| 8,034,264 B2 * | 10/2011 | Ritzberger | ............... | A61C 5/10 118/303 |
| 2010/0221683 A1 * | 9/2010 | Franke | .................. | C04B 41/009 433/215 |

FOREIGN PATENT DOCUMENTS

| | | |
|---|---|---|
| CN | 1287549 A | 3/2001 |
| CN | 1011778807 A | 7/2010 |
| CN | 101870582 A | 10/2010 |
| CN | 102228408 A | 11/2011 |
| CN | 102438964 A | 5/2012 |
| CN | 102674888 A | 9/2012 |

(Continued)

OTHER PUBLICATIONS

International Search Report, mailed Aug. 8, 2013, for PCT/CN2013/074962, 4 pages.

*Primary Examiner* — Carol M Koslow
(74) *Attorney, Agent, or Firm* — Seed IP Law Group LLP

(57) ABSTRACT

A coloring solution for dental zirconia ceramics and a method for using the same are provided. The coloring solution consists of coloring agents, a solvent, and an additive. The coloring agents are a combination of two or more rare earth metal compounds, wherein the rare earth metal compounds having rare earth metal ions selected from the group consisting of praseodymium (Pr) ions, erbium (Er) ions, cerium (Ce) ions, and neodymium (Nd) ions. The concentration of the rare earth metal ions in the solution is 0.05~3 mol/liter solvent. The molar ratio of Pr ions:Er ions:Ce ions:Nd ions in the solution is 1:(10~50):(0~20):(0~30).

11 Claims, 2 Drawing Sheets

(56) References Cited

FOREIGN PATENT DOCUMENTS

EP 2500009 * 9/2012
WO 00/15580 A1 3/2000

* cited by examiner

COLORING SOLUTION FOR DENTAL ZIRCONIA CERAMICS AND METHOD FOR USING THE SAME

TECHNICAL FIELD

The present invention relates to a dental coloring solution, especially to a coloring solution for dental zirconia ceramics, wherein the cations in the coloring solution are exclusively rare earth metal ions, and a method for using this coloring solution in the field of dentistry.

TECHNICAL BACKGROUND

In the prosthetic dentistry, the reproduction of the color and transmittance is a key parameter on determining the property of prosthesis and teeth. Before coloring, the color of zirconia ceramics per se generally is white to ivory. Though such a color can easily simulate the color of natural teeth, it is still not sufficient to meet the requirements for the color of the prosthesis in clinical. The clients are satisfied, only after adjusting the color and the transmittance of zirconia per se to be similar to those of the teeth to be repaired. One of the most important principles in the prosthetic dentistry is to obtain a combination of the mechanical property and aesthetics with the proviso that the tissue of teeth can be maintained as much as possible. After coloring, if the zirconia-based dental corona can show a color and lustre similar to that of natural teeth, the thickness of the veneering porcelain can be reduced or the veneering porcelain can be completely avoided in the process of preparing the prosthesis without losing the idea aesthetics, meanwhile the amount of the tissue removed for the teeth can be reduced, thus more tissue of the dental can be maintained.

Up to now, there are mainly two methods for coloring the zirconia prosthesis: one method is adding the coloring agent into the zirconia powder, preparing a colored green body from the colored zirconia powder, and then machining and sintering, to obtain a prosthesis having a color similar to that of natural teeth. The other method is formulating a specific coloring solution, soaking the machined and not colored zirconia-based dental corona in the coloring solution for a given period, e.g., several minutes, or brushing the coloring solution on the zirconia prosthesis, and then sintering to obtain a prosthesis having a color similar to that of the natural teeth.

WO2009/014903 (also published as CN 101778807 A) disclosed a coloring solution for coloring dental ceramics, the solution comprising a solvent and coloring agents. The coloring agents contain rare earth metals and transition metals or ions thereof. The concentration of the rare earth metals or ions thereof in the solution is from about 0.05 to about 1 mole/liter solvent. The concentration of the transition metals or ions thereof in the solution is from about 0.00001 to about 0.05 mole/liter solution. In this patent application, the dental ceramic is colored by the coloring solution so that a color similar to that of natural teeth is obtained. However, this patent application did not mention the adjustment of the transmittance of dental ceramics.

WO2004/110959 (also published as CN 1805913 A) disclosed a coloring solution for coloring the ceramic frameworks, the ceramic framework colored by the coloring solution and a method for obtaining a uniformly colored ceramic framework. The solution comprises solvent, metal salts and polyethylene glycol having a molecular weight Mn of 1000 to 200000, wherein the metal salts comprise rear earth metal and transition metal ions. The application also focused on the color adjustment of the ceramic frameworks, and did not mention the adjustment of the transmittance of the ceramic frameworks. The main principle of this application is preventing the metal ions from diffusing from the interior of the ceramic frameworks to the surface thereof by utilizing the polyethylene glycol having a molecular weight Mn of 1000 to 200000.

Merely adjusting the dental ceramic prosthesis to be similar to that of the natural teeth can not make the prosthesis having aesthetics effects of truly simulating the natural teeth. The inventors of the present invention found that to achieve the aesthetics effects of truly simulating the natural teeth, in addition to the color, the transmittance of the prostheses also need to be adjusted. Thus, there is a need for a dental prostheses of ceramics that has aesthetics effects of truly simulating the natural teeth. To this end, the present invention provides a coloring solution for dental ceramics, when applying to the dental zirconia ceramics, a dental zirconia ceramic having good color and transmittance can be obtained, and thus aesthetics effects of truly simulating the natural teeth can be achieved.

SUMMARY OF THE INVENTION

The present invention provides a coloring solution for dental zirconia ceramics, wherein the coloring solution consists of coloring agents, a solvent, and additives. The coloring agents are a combination of two or more rare earth metal compounds, wherein the rare earth metal compounds have rare earth metal ions selected from the group consisting of praseodymium (Pr) ions, erbium (Er) ions, cerium (Ce) ions, and neodymium (Nd) ions. Preferably the coloring agents are a combination of two or more soluble salts of rare earth metal compounds, the cations of the soluble salts are the rare earth metal ions selected from the group consisting of praseodymium (Pr) ions, erbium (Er) ions, cerium (Ce) ions, and neodymium (Nd) ions, and the anions of the soluble salts are one or more anions selected from the group consisting of chloride, acetate, nitrate, thiocyanate and sulfate. In the coloring solution of the present invention, the cations are exclusively the rare earth metal ions. In one embodiment, the molar ratio of Pr:Er:Ce:Nd is 1: (10-50): (0-10):(0~25), preferably the molar ratio of Pr:Er:Ce:Nd=1: (12~50):(1~10):(3~25).

The solvent is not specifically limited, provided that it can dissolve the coloring agents. For example, water and alcohols can be used either lonely or combined as the solvent. The alcohols preferably are these alcohols of small molecules having relatively high solubility in water, for example, methanol, ethanol, isopropanol, n-propanol, glycerol, and/or ethylene glycol.

The additives preferably are organic additives that do not leave any harmful residue after sintering. The additives comprise, but do not limit to, thixotropic agents, e.g., one or more selected from the group consisting of glucose, sucrose, polydextrose, polyethylene alcohol, and PEG (polyethylene glycol)-600; and surfactant, e.g., one or more selected from the group consisting of octylphenol polyoxyethylene ether, nonylphenol polyoxyethylene ether, polyoxyethylene fatty acid ester, polyoxyethylene amine In an embodiment, the concentration of the rear earth metal ions in the solutions is 0.05 to 3 mole/liter solvent.

In an embodiment, the amount of the additives is 0 to 50 wt %, based on the total weight of the coloring solution.

The present invention also relates to a method for treating a pre-sintered body of the zirconia ceramics with the coloring solutions of the present invention to produce dental ceramics with simulating the color of teeth, comprising the following steps:

step 1: preparing a coloring solution according to the present invention and the pre-sintered body of the zirconia ceramics;

step 2: treating the pre-sintered body of the zirconia ceramics with the coloring solution;

step 3: drying the treated pre-sintered body of the zirconia ceramics;

step 4: sintering the dried pre-sintered body of the zirconia ceramics at high temperature.

In an embodiment, the coloring solution is prepared by, e.g., dissolving the soluble salts of the rare earth metal ions in a solvent. The coloring solution of the present invention can be prepared via any methods known in the prior art. During the dissolving, conventional methods, e.g., stirring, and heating, can be used to accelerate the dissolving of the soluble salts.

Hereinafter, "the pre-sintered body of the zirconia ceramics" refers to any pre-sintered body of the zirconia ceramics known in the prior art, e.g., the body of zirconia ceramics pre-sintered at a temperature of from 800 to 1200° C., such as, the body of the tetragonal zirconia polycrystal (TZP) ceramics, or body of tetragonal and cubic mixed zirconia ceramics etc. In the present invention, there is no specific limitation to the composition and crystal form of the pre-sintered body of the zirconia ceramics, provided that the strength requirements for the dental ceramic material are met. Additionally, the green body of the zirconia ceramics can also be used directly in step 2 of the method of the present invention, if the shaped green body of the zirconia ceramics can be properly machined and treated with the coloring solution of the present invention. The pre-sintered body of the zirconia ceramics usually has a porosity of about 40%-70%, preferably about 50%.

The pre-sintered body of the zirconia ceramics can be the pre-sintered body of the zirconia ceramics after or before machining. The pre-sintered body of the zirconia ceramics preferably is machined according to the requirements for teeth. Herein, machining means to machine the pre-sintered body of the ceramics to a dental blank which is augmented according to the desired shape and size for teeth, via mechanical methods, e.g., cutting and chipping etc. After sintering, a dental prosthesis having desired shape and size can be obtained.

In step 2, the method for treating the pre-sintered body of the zirconia ceramics can be any method known in the prior art, including, but not limited to, soaking the pre-sintered body of the zirconia ceramics in the coloring solution; or brushing, spraying or spin coating the coloring solution on the pre-sintered body of the zirconia ceramics; or applying the coloring solution the pre-sintered body of the zirconia ceramics via sponge. The above methods can be used separately or in combination.

The applying amount of the coloring solution of the present invention on the pre-sintered body of the zirconia ceramics is not specifically limited, and can be selected by a person skilled in the art empirically, provided that the desired color can be obtained.

In step 3, the drying can be performed via any known drying method in the prior art, for example, including, but not limited to, drying at room temperature, infrared drying, freeze drying, or microwave drying etc. The period for drying is not specifically limited, provided that the solvents can be removed substantially. A person skilled in the art can select a proper drying period empirically for various drying methods.

In step 4, the temperature for sintering at high temperature is from 1300 to 1700° C., preferably from 1480 to 1600° C. The period for heating is preferably 0.5 to 3 h, more preferably 2 h. The sintering device is not specifically limited. Any sintering devices known in the prior art can be used, e.g., box-type electric furnace, tube furnace, pushed bat kiln etc. The atmosphere for the sintering of the present invention is not specifically defined, and any atmosphere that is favorable for the color development of the coloring agents can be used, preferably air atmosphere.

The dental ceramic prosthesis obtained after drying and sintering the pre-sintered green body of the zirconia ceramic treated by the coloring solution of the present invention shows aesthetic effects and appearance similar to that of the natural teeth. The inventors surprisingly found that, by deliberately selecting the compounds of specific rare earth metal elements as coloring agent, the present invention can obtain a dental ceramic prosthesis not only having a color similar to that of the natural teeth but also having very good transmittance, so that the dental ceramic prosthesis as a whole have the aesthetic effects of truly simulating the natural teeth.

Without being bound to any theory, the inventors hold that, these deliberately selected rare earth metal elements have the ion diameter close to that of the zirconium ions, thus they, especially the Pr ions, Er ions, Nd ions, and Ce ions, preferably Pr ions and Er ions, can enter into the crystal lattice of zirconia instead of maintaining at the crystal boundary of the zirconia ceramics. As a result, the transmittance of the zirconia ceramics can be improved. To the contrary, the transition metals used in the prior art have an ion diameter substantially different from the diameter of the zirconium ions, so that they can not enter into the crystal lattice of the zirconia, and can only maintain at the crystal boundary. The transition metal ions maintained at the crystal boundary can scatter the incident light easily, so that the transmittance of the ceramic decreases. In addition, because the rare earth metal ions can enter into the crystal lattice of the zirconia, the phase transfer from tetragonal phase to cubic phase of zirconia can be promoted. Since the cubic phase of zirconia has a transmittance higher than that of the tetragonal phase, this may form another reason that the transmittance of the zirconia can be enhanced via rare earth metal ions.

The inventors further surprisingly found that, the coloring solution of the present invention is stable for a long period without adding a stabilizing agent or a complexing agent. Without being bounded to any theory, the reason might be that comparatively higher pH value is needed for the hydrolysis of the rare earth metal ions, so that the stability of the solution can also be improved correspondingly.

Moreover, the zirconia ceramic prosthesis treated by the coloring solution of the present invention shows a more uniform color. The reason might be that the rare earth metal ions have a relative big diameter, so that they diffuse slowly to the surface of the ceramic body along with the evaporation of the water during drying after penetrating into the pre-sintered zirconia ceramics. As a result, the rare earth metal ions uniformly maintained in the pre-sintered body of the zirconia ceramics, or maintained in a higher depth from the surface of the pre-sintered body of the zirconia ceramics, so that the ceramic prosthesis as a whole shows a more uniform color.

DETAILED DESCRIPTION OF THE EMBODIMENTS

Figure 1:
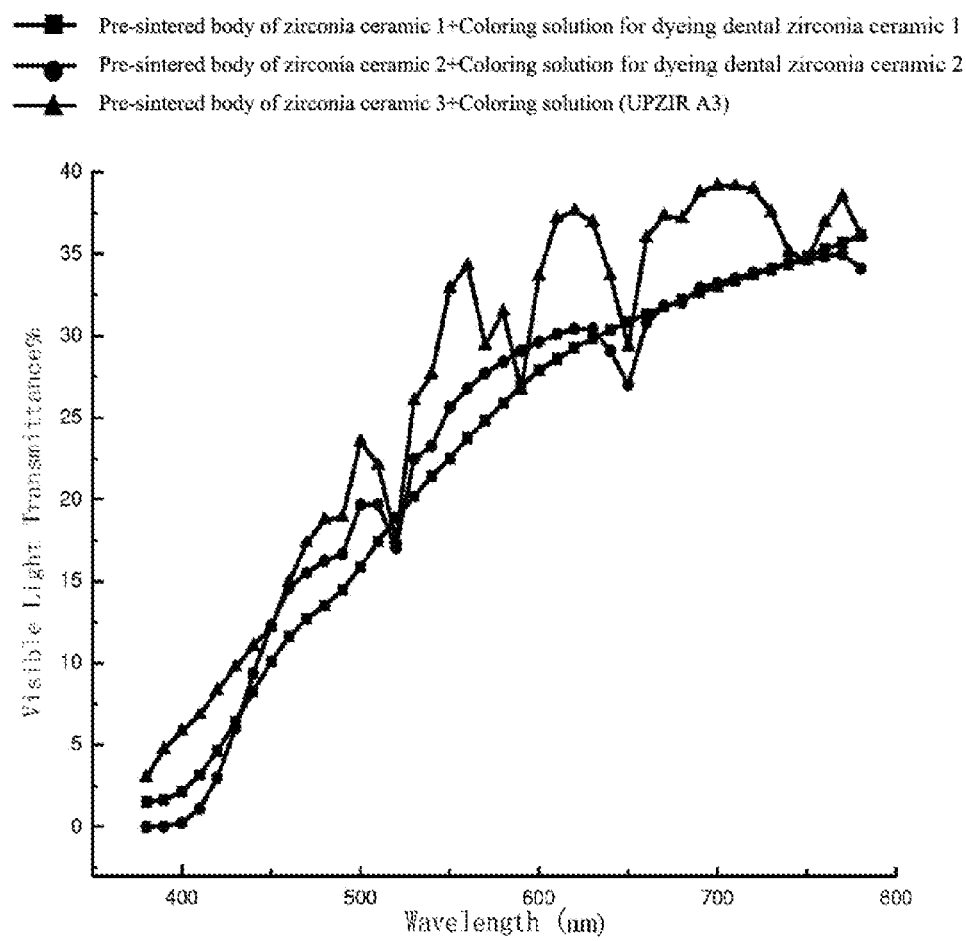
FIG. 1 shows the visible light transmittance of the samples obtained in example 6 of the present invention and comparative examples 1 and 2, wherein the different bodies of the pre-sintered zirconia ceramics are colored with three different coloring solutions, after sintering, all of the samples show a substantially same color.

Hereafter, some specific embodiments of the present invention will be described in detail, with reference to the examples and figures. However, the examples described are only some illustrated examples of the present invention, not all of the examples of the present invention. Based on the examples provided herein, all of the other examples, obtainable for a person skilled in the art without any creative work, are also fall within the scope of protection of the present invention.

EXAMPLE 1

A coloring solution containing $Pr(NO_3)_3$ and $Er(NO_3)_3$ was prepared, wherein the concentration of $Pr(NO_3)_3$ was 0.005 mole/liter, and the concentration of $Er(NO_3)_3$ is 0.060 mole/liter. Water was used as solvent. Polydextrose is added to the aqueous solution in a concentration of 10 wt %, based on the total weight of the solution. In this solution, the molar ratio of Pr:Er is 1:12.

A zirconia ceramic body having a porosity of 50% was prepared by shaping a 3Y-TZP powder via isostatic pressing, and then sintering at 1000° C. for 2 hours.

The coloring solution prepared was brushed on the pre-sintered body of the zirconia ceramics by using a writing brush. The coloring solution was brushed for 7 times in total.

The coated pre-sintered body of the zirconia ceramics was infrared dried for 20 minutes, and then sintered in a box-type electric furnace at a temperature of 1600° C. for 1.5 hour. A colored dental prosthesis was obtained.

EXAMPLE 2

A coloring solution, containing $PrCl_3$ of 0.009 mole/liter solvent, $ErCl_3$ of 0.153 mole/liter solvent, and $NdCl_3$ of 0.027 mole/liter solvent as coloring agents, was prepared. Water was used as solvent. Glucose was added into the aqueous solution, as an additive, in a concentration of 30 wt %, based on the total weight of the solution. In this solution, the molar ratio of Pr:Er:Nd is 1:17:3.

A pre-sintered body of zirconia ceramics was prepared as in example 1.

The coloring solution was applied on the pre-sintered body of the zirconia ceramics with a sponge, until the coloring solution can not permeate into the colored green body any more.

The coated body of the zirconia ceramics was freeze dried at −30° C. for 3 hours, then sintered in a box-type electric furnace at a temperature of 1500° C. for 3 hours. A colored dental prosthesis according to the present example was obtained.

EXAMPLE 3

A coloring solution, containing $PrAc_3$ of 0.015 mole/liter solvent, $ErAc_3$ of 0.252 mole/liter solvent, and $NdAc_3$ of 0.107 mole/liter solvent as coloring agents, was prepared. Water was used as solvent. PEG-600 was added as an additive, with a concentration of 25 wt %, based on the total weight of the solution. In this solution, the molar ratio of Pr:Er:Nd is 1:16.8:7.1.

A pre-sintered body of zirconia ceramics was prepared as in example 1. The pre-sintered body of zirconia ceramics was soaked in the coloring solution for 5 minutes.

The soaked body of the zirconia ceramics was dried at room temperature for 2 hours, then sintered in a box-type electric furnace at a temperature of 1480° C. for 2 hours. A dental prosthesis according to the present example was obtained.

EXAMPLE 4

A coloring solution, containing $Pr(NO_3)_3$ of 0.018 mole/liter solvent, $Er(NO_3)_3$ of 0.262 mole/liter solvent, and $Nd(NO_3)_3$ of 0.092 mole/liter solvent as coloring agents, was prepared. Water was used as solvent. Sucrose was added as additive, with a concentration of 20 wt %, based on the total weight of the solution. In this solution, the molar ratio of Pr:Er:Nd is 1:14.6:5.1.

A pre-sintered green body of zirconia ceramic was prepared as in example 1, and then brushed the coloring solution prepared in the present example for 2 or 3 times. Then, the coloring solution was further sprayed on the green body until the zirconia ceramic body was saturated by the coloring solution.

The coated body of the pre-sintered zirconia ceramics was dried via microwave for 15 minutes, then sintered in a box type electric furnace at a temperature of 1700° C. for 0.5 hour. A dental prosthesis according to the present example was obtained.

EXAMPLE 5

A coloring solution, containing $PrCl_3$ of 0.035 mole/liter solvent, $ErCl_3$ of 0.438 mole/liter solvent, and $NdCl_3$ of 0.211 mole/liter solvent as coloring agents, was prepared. Water was used as solvent. PEG was added as an additive, with a concentration of 15 wt %, based on the total weight of the solution. In this solution, the molar ratio of Pr:Er:Nd is 1:12.5:6.0.

Then the related steps in example 1 were carried out. A dental prosthesis according to the present example was obtained.

EXAMPLE 6

A coloring solution, containing $Er(NO_3)_3$ of 0.40 mole/liter solvent, $Pr(NO_3)_3$ of 0.01 mole/liter solvent, $Ce(NO_3)_3$ of 0.01 mole/liter solvent, and $Nd(NO_3)_3$ of 0.1 mole/liter solvent as coloring agents, was prepared. Water was used as solvent. Polydextrose was added as an additive, with a concentration of 20 wt %, based on the total weight of the solution. In this solution, the molar ratio of Pr:Er:Ce:Nd is 1:40:1:10.

Then the related steps in example 1 were carried out. A dental prosthesis according to the present example was obtained.

EXAMPLE 7

A coloring solution, containing $Er(NO_3)_3$ of 0.30 mole/liter solvent, $Pr(NO_3)_3$ of 0.01 mole/liter solvent, $Ce(NO_3)_3$ of 0.10 mole/liter solvent, and $Nd(NO_3)_3$ of 0.10 mole/liter solvent as coloring agents, was prepared. Water was used as solvent. Polydextrose was added as an additive, with a concentration of 20 wt %, based on the total weight of the solution. In this solution, the molar ratio of Pr:Er:Ce:Nd is 1:30:10:10.

Then the related steps in example 1 were carried out. A dental prosthesis according to the present example was obtained.

EXAMPLE 8

A coloring solution, containing $Er(NO_3)_3$ of 0.20 mole/liter solvent, $Pr(NO_3)_3$ of 0.01 mole/liter solvent, $Ce(NO_3)_3$ of 0.05 mole/liter solvent, and $Nd(NO_3)_3$ of 0.25 mole/liter solvent as coloring agents, was prepared. Water was used as the solvent. Polydextrose was added as the additive, with a concentration of 20 wt %, based on the total weight of the solution. In this solution, the molar ratio of Pr:Er:Ce:Nd is 1:20:5:25.

Then the related steps in example 1 were carried out. A dental prosthesis according to the present example was obtained.

COMPARATIVE EXAMPLES 1 and 2

The steps of example 1 were repeated with the exception that a commercial coloring solution for dyeing dental zirconia ceramic 1 sold under the trade name PRETTAU® AQUARELL A3 (ZIRKONZAHN) and a commercial coloring solution for dyeing dental zirconia ceramic 2 sold under the trade name LAVA™ PLUS HIGH TRANSLUCENCY ZIRCONIA DYEING LIQUID A3 (3M ESPE) were used instead of the coloring solution prepared in example 1, to obtain the samples of comparative examples 1 and 2 respectively.

COMPARATIVE EXAMPLE 3

A coloring solution, containing $Ce_2(SO_4)_3$ of 1.230 mole/liter solvent, $Gd_2(SO_4)_3$ of 0.635 mole/liter solvent, and $Te_2(SO_4)_3$ of 1.135 mole/liter solvent as coloring agents, was prepared. Ethylene glycol was used as the solvent. Polyethylene alcohol with a concentration of 30 wt % was used as the additives, based on the total weight of the solution. In this solution, the molar ratio of Ce:Gd:Te is 1.9:1:1.8.

Then the related steps in example 1 were carried out. A dental prosthesis according to this comparative example was obtained.

COMPARATIVE EXAMPLE 4

A coloring solution, containing $CeCl_3$ of 1.031 mole/liter solvent, $EuCl_3$ of 0.125 mole/liter solvent, and $NdCl_3$ of 1.335 mole/liter solvent as coloring agents, was prepared. A 1:1 mixture of ethanol and water was used as the solvent. PEG 1000 with a concentration of 15 wt % was used as the additives, based on the total weight of the solution. In this solution, the molar ratio of Ce:Eu:Nd is 8.25:1:10.68.

Then the related steps in example 1 were carried out. A dental prosthesis according to this comparative example was obtained.

Both the color and the appearance (e.g., the transmittance) of the dental prostheses prepared according to comparative examples 3 and 4 fail to meet the requirements of the dental prosthesis in clinical.

Measurement and Evaluation

Bend strength of the samples of examples 1 to 8 and comparative examples 1 to 4 were measured by three-point bending method. The size of samples is that, width: (4±0.2) mm; thickness (1.2±0.2) mm, and length: above 20 mm.

Measuring method: Cross section size of each sample was measured, with accuracy of ±0.01. Span distance was adjusted to 16 mm. A sample was placed in the center of the supporting point of the jig, a load was applied on the surface of the sample in direction vertical to the long axis of the sample. The load was applied by the test machine with a speed of (1.0±0.5) mm/minute until the sample broke. The load on breaking was recorded.

Three-point bending strength M of each sample was calculated according to the following equation:

$$M = \frac{3WL}{2bd^2}$$

wherein:
M—Bending Strength, MPa;
W—the maximum load on the sample until broken, N;
L—span distance, mm;
b—width of the sample, mm;
d—thickness of the sample, mm.

Lambde 650 ultraviolet-visible spectrophotometer was used to determine the transmittance of the samples, the wavelength is in a range of from 380 to 780 nm. The visible transmittance of the samples of examples 1 to 8 and comparative examples 1-4 were measured.

Size of the sample: diameter of above 25 mm and thickness of 1.0±0.01 mm.

The measured bending strengths and transmittances were listed in below table 1.

TABLE 1

The three-point bending strengths and transmittances of the sample of zirconia colored by the different coloring solutions

| | Coloring agents (mol/L) | Solvent | Additives wt % | three-point bending strength MPa | Visible light transmittance % |
|---|---|---|---|---|---|
| blank | no | No | no | 1371 | 42.93 |
| example 1 | $Pr(NO_3)_3$ 0.005 $Er(NO_3)_3$ 0.060 | water | polydextrose 10 | 1248 | 42.15 |

TABLE 1-continued

The three-point bending strengths and transmittances of the sample of zirconia colored by the different coloring solutions

|  | Coloring agents (mol/L) | Solvent | Additives wt % | three-point bending strength MPa | Visible light transmittance % |
|---|---|---|---|---|---|
| example 2 | PrCl$_3$ 0.009<br>ErCl$_3$ 0.153<br>NdCl$_3$ 0.027 | water | Glucose<br>30 | 1157 | 40.88 |
| example 3 | PrAc$_3$ 0.015<br>ErAc$_3$ 0.252<br>NdAc$_3$ 0.107 | water | PEG 600<br>25 | 1182 | 39.78 |
| example 4 | Pr(NO$_3$)$_3$ 0.018<br>Er(NO$_3$)$_3$ 0.262<br>Nd(NO$_3$)$_3$ 0.092 | water | sucrose<br>20 | 1139 | 39.50 |
| example 5 | PrCl$_3$ 0.035<br>ErCl$_3$ 0.438<br>NdCl$_3$ 0.211 | water | PEG<br>15 | 1092 | 38.69 |
| example 6 | Pr(NO$_3$)$_3$ 0.01<br>Ce(NO$_3$)$_3$ 0.01<br>Er(NO$_3$)$_3$ 0.4<br>Nd(NO$_3$)$_3$ 0.1 | water | polydextrose<br>20 | 1289 | 38.50 |
| example 7 | Er(NO$_3$)$_3$: 0.30,<br>Pr(NO$_3$)$_3$: 0.01,<br>Ce(NO$_3$)$_3$: 0.10,<br>Nd(NO$_3$)$_3$: 0.10 | water | polydextrose<br>20 | 1089 | 39.0 |
| example 8 | Er(NO$_3$)$_3$: 0.20,<br>Pr(NO$_3$)$_3$: 0.01,<br>Ce(NO$_3$)$_3$: 0.05,<br>Nd(NO$_3$)$_3$: 0.25 | water | polydextrose<br>20 | 1154 | 39.4 |
| comparative example 1 | Coloring solution for dyeing dental zirconia ceramic 1 (PRETTAU ® AQUARELL A3 (ZIRKONZAHN )) |  |  | 1135 | 26.8 |
| comparative example 2 | Coloring solution for dyeing dental zirconia ceramic 2 (LAVA ™ PLUS HIGH TRANSLUCENCY ZIRCONIA DYEING LIQUID A3 (3M ESPE)) |  |  | 1131 | 30.1 |
| comparative example 3 | Ce$_2$(SO$_4$)$_3$ 1.230<br>Gd$_2$(SO$_4$)$_3$ 0.635<br>Te$_2$(SO$_4$)$_3$ 1.135 | ethylene glycol | polyethylene alcohol<br>30 | 989 | 36.86 |
| comparative example 4 | CeCl$_3$ 1.031<br>EuCl$_3$ 0.125<br>NdCl$_3$ 1.335 | water, ethanol | PEG 1000<br>15 | 953 | 35.94 |

Notes
Visible light transmittance = transmittance at wavelength of 550 nm × 1.19;

The blank sample is that obtained by subjecting the pre-sintered zirconia of example without treating by the coloring solution to the sintering process of example 1.

To evaluate the appearance of the obtained dental prosthesis, 20 ordinary persons with good eyesight ranging from 25 to 40 years old were randomly selected. Appearance of the dental prostheses samples obtained in examples 1 to 8 and comparative examples 1-4 were evaluated and scored by these peoples. The samples were scored as 0 to 5, wherein the sample having appearance most close to the natural teeth is scored as 5, and the blank sample is scored as 0. The samples that having intermediate appearance are correspondingly scored according to the degree that their appearance is close to that of the natural teeth, wherein, the more their appearance closes to that of the natural teeth, the higher score is given. All of the results given by these 20 peoples were averaged, and listed in table 2.

TABLE 2

Scores of the appearance of the samples.

|  | average score |
|---|---|
| example 1 | 4.5 |
| example 2 | 4.7 |
| example 3 | 4.65 |
| example 4 | 4.65 |
| example 5 | 4.8 |
| example 6 | 4.9 |
| example 7 | 4.95 |
| example 8 | 4.85 |
| comparative example 1 | 3.9 |
| comparative example 2 | 4.1 |
| comparative example 3 | 3.5 |
| comparative example 4 | 3.3 |

FIG. 1 shows the comparison of the transmittance of the samples obtained by using a commercial coloring solution for dyeing dental zirconia ceramic 1 sold under the trade name PRETTAU® AQUARELL A3 (ZIRKONZAHN), a commercial coloring solution for dyeing dental zirconia ceramic 2 sold under the trade name LAVA™ PLUS HIGH TRANSLUCENCY ZIRCONIA DYEING LIQUID A3 (3M ESPE), and the coloring solution prepared in example 6 of the present invention (UPZIR A3). In FIG. 1, pre-sintered body of zirconia ceramic 1 (sold under the trade name PRETTAU® ZIRCONIA (ZIRKONZAHN)), pre-sintered body of zirconia ceramic 2 (sold under the trade name LAVA™ PLUS HIGH TRANSLUCENCY ZIRCONIA (3M ESPE)) and pre-sintered body of zirconia ceramic 3 (sold under the trade name UPCERA ST (UPCERA)) were used, and the three kinds of samples of dental prosthesis obtained therefrom showed a substantially same color. After chemical analysis, it is proved that both of two kinds of commercial solutions contain ions of transitional metals. It can be seen from FIG. 1 that, highest visible light transmittance was obtained by using the coloring solution according to example 6 of the present invention.

Figure 2:
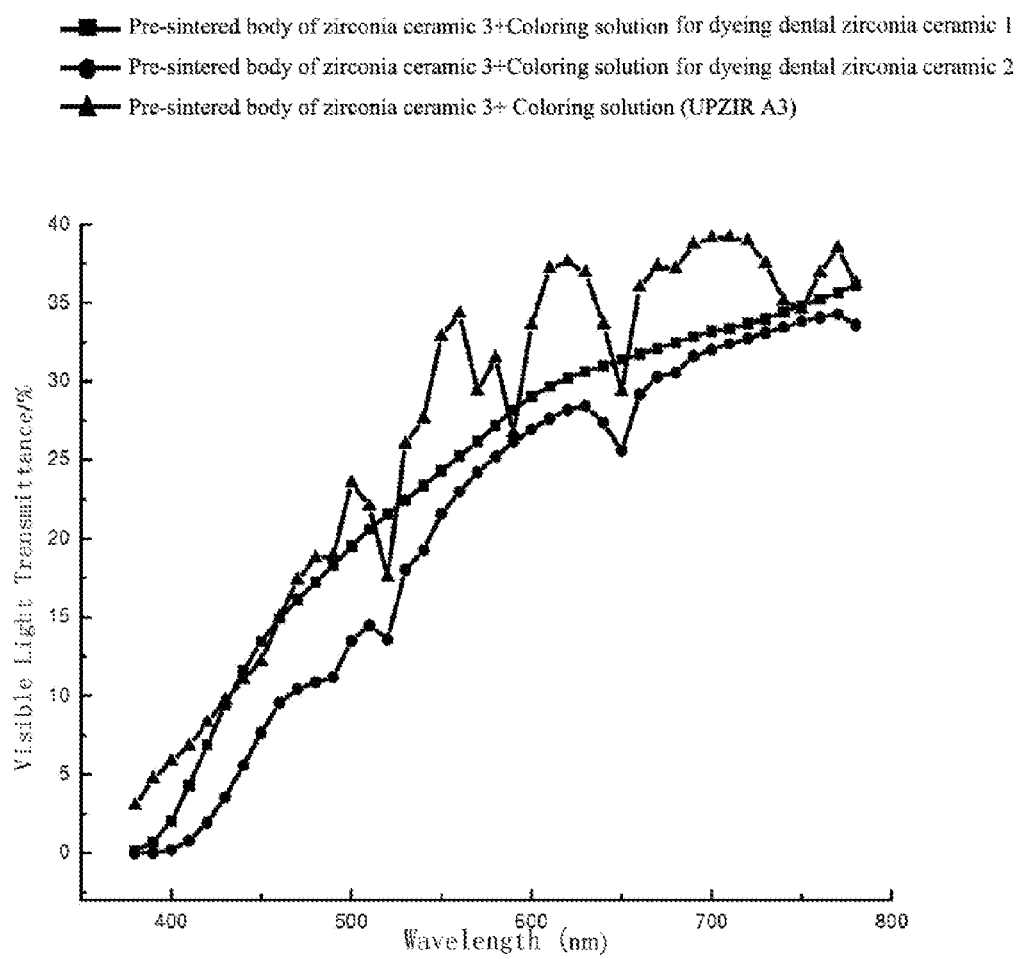
FIG. 2 shows the visible light transmittance of the samples obtained in example 6 of the present invention and comparative examples 1 and 2, wherein the same bodies of the pre-sintered zirconia ceramics are colored with three different coloring solutions, after sintering, all of the samples show a substantially same color.

FIG. 2 shows that the samples of the dental prosthesis, obtained by treating the pre-sintered body of zirconia, UPCERA ST dental corona, with the coloring solution of the present invention (UPZIR A3) and the commercial coloring solution for dyeing dental zirconia ceramic 1 sold under the trade name PRETTAU® AQUARELL A3 (ZIRKONZAHN) and commercial coloring solution for dyeing dental zirconia ceramic 2 sold under the trade name LAVA™ PLUS HIGH TRANSLUCENCY ZIRCONIA DYEING LIQUID A3 (3M ESPE), have a similar color. It can be seen from FIG. 2 that, the highest visible light transmittance was obtained by using the coloring solution according to the present invention.

Some specific examples are described hereinbefore. These examples are for the purpose of clearly illustrating the present invention, not for limiting the scope of protection of the present invention. Without going beyond the spirit and principle of the present invention, any modification, substitution, and improvement etc, fall within the scope of the present invention.

The invention claimed is:

1. A coloring solution for dental zirconia ceramics, the coloring solution consists of coloring agents, a solvent, and an additive,
wherein the coloring agents are a combination of two or more rare earth metal compounds, wherein the rare earth metal compounds having rare earth metal ions selected from the group consisting of praseodymium (Pr) ions, erbium (Er) ions, cerium (Ce) ions, and neodymium (Nd) ions,
the concentration of the rare earth metal ions in the coloring solution is 0.05~3 mol/liter solvent, and in the solution, the molar ratio of Pr ions:Er ions:Ce ions:Nd ions is 1:(10~50):(0~20):(0~30);
the solvent is one selected from the group consisting of water, methanol, ethanol, isopropanol, n-propanol, glycerol, and ethylene glycol, or mixture of two or more thereof, and
the amount of the additive is 0-50 wt %, based on the total weight of the coloring solution.

2. The coloring solution for dental zirconia ceramics according to claim 1, characterized in that, Pr ions:Er ions:Ce ions:Nd ions is 1:(12~40):(1~10):(3~25).

3. The coloring solution for dental zirconia ceramics according to claim 1, characterized in that, the coloring agents are a combination of soluble salts of the rare earth metal ions, and one or more anions selected from the group consisting of chloride, acetate, nitrate, thiocyanate and sulfate.

4. The coloring solution for dental zirconia ceramics according to claim 1, characterized in that, the additive comprises thixotropic agent which includes one or more selected from the group consisting of glucose, sucrose, polydextrose, polyethylene alcohol, and PEG-600.

5. The coloring solution for dental zirconia ceramics according to claim 1, characterized in that, the additive comprises surfactant which includes one or more selected from the group consisting of octylphenol polyoxyethylene ether, nonylphenol polyoxyethylene ether, polyoxyethylene fatty acid ester, polyoxyethylene amine.

6. A method of using the coloring solution for dental zirconia ceramics according to claim 1, characterized in that, the method comprises the steps of:
step 1: preparing the coloring solution and a pre-sintered body of zirconia ceramics;
step 2: treating the pre-sintered body of the zirconia ceramics with the coloring solution;
step 3: drying the treated pre-sintered body of the zirconia ceramics;
step 4: sintering the dried pre-sintered body of the zirconia ceramics at high temperature.

7. The method of claim 6, characterized in that, the treating of the pre-sintered body of the zirconia ceramics is performed by soaking the pre-sintered body of the zirconia ceramics in the coloring solution; or by brushing, spraying or spin coating the coloring solution on the pre-sintered body of the zirconia ceramic; or by applying the coloring solution on the pre-sintered body of the zirconia ceramics via sponge, or any combination thereof.

8. The method of claim 6, characterized in that, the drying is performed by drying at room temperature, infrared drying, freeze drying, or microwave drying.

9. The method of claim 6, characterized in that, the sintering temperature for sintering at high temperature is from 1300 to 1700° C. and the sintering period is 0.5 to 3 h.

10. The method of claim 9, characterized in that, the sintering temperature for sintering at high temperature is from 1480 to 1600° C.

11. The method of claim 9, characterized in that, the sintering period is 2 h.

\* \* \* \* \*